United States Patent [19]

Hutchison

[11] Patent Number: 4,533,667
[45] Date of Patent: Aug. 6, 1985

[54] IMIDAZOLIDINEDIONE DERIVATIVES

[75] Inventor: Alan J. Hutchison, Verona, N.J.

[73] Assignee: Pfizer Inc., New York, N.Y.

[21] Appl. No.: 600,759

[22] Filed: Apr. 16, 1984

Related U.S. Application Data

[62] Division of Ser. No. 497,962, May 25, 1983, Pat. No. 4,464,380.

[51] Int. Cl.³ ............... A61K 31/41; C07D 471/20; C07D 487/10
[52] U.S. Cl. .................. 514/278; 514/387; 546/15; 548/309
[58] Field of Search ............ 346/15; 548/309; 424/256, 274

[56] References Cited

U.S. PATENT DOCUMENTS 3,821,383  6/1974  Sestanj et al. .............. 424/258
4,200,642  4/1980  Schnur ......................... 424/272
4,443,465  4/1984  Brittain et al. ............... 424/273 R

FOREIGN PATENT DOCUMENTS 0028906  5/1981  European Pat. Off. ........ 548/309

OTHER PUBLICATIONS

H. Otomasu et al., "Spiro Heterocyclic Compounds, I. Synthesis of Spiro-[imidazoline-4,3'-indoline]-2,2',5-triones", *Chem. Pharm. Bull.*, (Tokyo), vol. 23, No. 7, p. 1431, (1975).

*Primary Examiner*—Robert T. Bond
*Attorney, Agent, or Firm*—Charles J. Knuth; Peter C. Richardson

[57] ABSTRACT

A series of novel spiro-oxindole imidazolidinedione derivatives have been prepared, including their pharmaceutically acceptable salts. These compounds are useful in therapy as aldose reductose inhibitors for the control of certain chronic diabetic complications. Preferred compounds include 6'-amino-spiro-[imidazolidine-4,3'-indoline]-2,2',5-trione, 5'-chloro-7'-aminospiro-[imidazolidine-4,3'-indoline]-2,2',5-trione, 1'-(3-pyridylmethyl)-5'-fluoro-spiro-[imidazolidine-4,3'-indoline]-2,2',5-trione, 1'-(3-pyridylmethyl)-5',7'-dichloro-spiro-[imidazolidine-4,3'-indoline]-2,2',5-trione and spiro-[imidazolidine-4,3'-(6-azaindoline)]-2,2',5-trione. Methods for preparing these compounds from known starting materials are provided.

19 Claims, No Drawings

IMIDAZOLIDINEDIONE DERIVATIVES

This is a division, of application Ser. No. 497,962, filed on May 25, 1983, now U.S. Pat. No. 4,464,380.

BACKGROUND OF THE INVENTION

This invention relates to new imidazolidinedione derivatives of interest to those in the field of medicinal chemistry and chemotherapy. More particularly, it is concerned with a novel series of spiro-oxindole imidazolidinedione compounds for the control of certain chronic complications arising from diabetes mellitus (e.g., diabetic cataracts, retinopathy and neuropathy).

Past attempts to obtain new and better oral antidiabetic agents have, for the most part, involved an endeavor to lower blood sugar levels. However, little is known about the effect of organic compounds in preventing or arresting certain chronic complications of diabetes, such as diabetic cataracts, neuropathy and retinopathy, etc. Nevertheless, K. Sestanj et. al. in U.S. Pat. No. 3,821,383 do disclose that certain aldose reductase inhibitors like 1,3-dioxo-1H-benz[d,e]isoquinoline-2(3H)-acetic acid and some closely-related derivatives thereof are useful for these purposes even though they are not known to be hypoglycemic. These compounds function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of diabetic subjects are prevented or reduced. As a result, these compounds control certain chronic diabetic complications, including those of an ocular nature, since it is already known in the art that the presence of polyols in the lens of the eye leads to cataract formation and concomitant loss of lens clarity.

SUMMARY OF THE INVENTION

The present invention relates to novel spiro-oxindole imidazolidinedione compounds useful in therapy as aldose reductase inhibitors for the control of certain chronic complications arising in a diabetic subject. More specifically, the novel compounds of this invention are selected from the group consisting of spirohydantoin derivatives of the formulae:

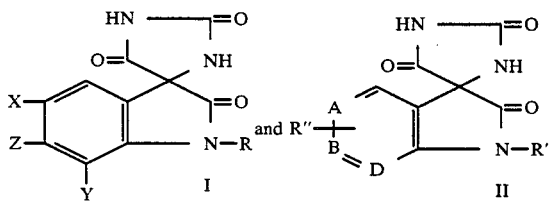

and the pharmaceutically acceptable salts thereof, wherein X and Y are each hydrogen, fluorine, chlorine, bromine, nitro or amino; Z is hydrogen or amino, with the proviso that Z is always other than amino when at least one of X and Y is other than hydrogen; R is a member selected from the group consisting of hydrogen, aryl and aralkyl having up to three carbon atoms in the alkyl moiety wherein each of said aryl moieties is chosen from the group consisting of pyridyl and ring-substituted pyridyl, with each ring substituent being chosen from the group consisting of fluorine, chlorine, bromine and alkyl having from one to four carbon atoms, with the proviso that said R is always other than hydrogen when each of X, Y and Z is other than amino; =A—B=D— of formula II represents =N—CH=CH—, =CH—CH=N— or =CH—N=CH—; R' is a member selected from the group consisting of hydrogen, alkyl having from one to four carbon atoms, aryl and aralkyl having up to three carbon atoms in the alkyl moiety wherein each of said aryl moieties is chosen from the group consisting of pyridyl, thienyl, phenyl and mono and di-substituted phenyl, with each ring substituent being chosen from the group consisting of fluorine, chlorine, bromine, alkyl and alkoxy each having up to four carbon atoms and trifluoromethyl; and R'' is hydrogen, hydroxy, fluorine, chlorine, alkyl or alkoxy each having up to four carbon atoms or trifluoromethyl. These novel compounds are aldose reductase inhibitors and therefore, possess the ability to reduce or inhibit sorbitol accumulation in the lens and peripheral nerves of diabetic subjects.

One group of compounds of interest of the present invention is that of formula I wherein X is fluorine, Y and Z are each hydrogen and R is pyridylalkyl having up to three carbon atoms in the alkyl moiety. Another group of compounds of interest of the present invention is that of formula I wherein X and Y are each chlorine, Z is hydrogen and R is pyridylalkyl having up to three carbon atoms in the alkyl moiety.

A further group of compounds of interest of the present invention is that of formula II wherein =A—B=D— is =CH—N=CH— and R'' is hydrogen or alkyl having up to four carbon atoms (e.g., methyl). Preferably, R' is hydrogen, alkyl having from one to four carbon atoms (e.g., isopropyl), mono-substituted phenylalkyl having up to three carbon atoms in the alkyl moiety (e.g., p-fluorobenzyl or p-chlorobenzyl), di-substituted phenylalkyl having up to three carbon atoms in the alkyl moiety (e.g., 3,4-dichlorobenzyl) or mono-substituted phenyl (e.g., p-fluorophenyl).

Of special interest in this connection are such typical and preferred member compounds of the invention as 6'-amino-spiro-[imidazolidine-4,3'-indoline]-2,2',5-trione, 5'-chloro-7'-amino-spiro[imidazolidine-4,3'-indoline]-2,2', 5-trione, 1'-(3-pyridylmethyl)-5,'-fluoro-spiro-[imidazolidine-4,3'-indoline]-2,2',5-trione, 1'-(3-pyridylmethyl)-5,7'-dichloro-spiro-[imidazolidine-4,3'-indoline]-2,2',5-trione and spiro-[imidazoline-4,3'-(6-azaindoline)]-2,2',5-trione, respectively. These particular compounds are highly potent as regards their aldose reductose inhibitory activity.

DETAILED DESCRIPTION OF THE INVENTION

In accordance with the process employed for preparing the novel compounds of this invention (viz., those of structural formulae I-II), an appropriately substituted carbonyl ring compound of structural formulae III or IV as respectively set forth below:

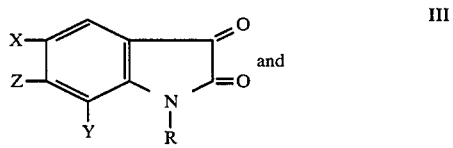

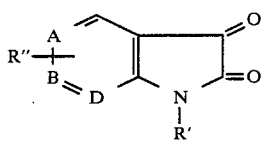

wherein X,Y,Z,R,R' and R" are each as previously defined (with proviso), is condensed with an alkali metal cyanide (e.g. sodium cyanide or potassium cyanide) and ammonium carbonate to form the desired spiro-oxindole imidazolidinedione final product of the structural formulae previously indicated. This particular reaction is normally carried out in the presence of a reaction-inert polar organic solvent medium in which both the reactants and reagents are mutually miscible. Preferred organic solvents for use in this connection include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylformamide, N,N-diethylformamide and N,N-dimethylacetamide, etc. In general, the reaction is conducted at a temperature that is in the range of from about 50° C. up to about 150° C. for a period of about two hours to about four days. Although the amount of reactant and reagents employed in the reaction can vary to some extent, it is preferable to employ at least a slight molar excess of the alkali metal cyanide reagent with respect to the carbonyl ring compound starting material in order to effect maximum yield. In this way, for example, 1-(3-pyridylmethyl)-5-fluoroindoline-2,3-dione is converted to 1'-(3-pyridylmethyl)-5'-fluoro-spiro[imidazolidine-4,3'-indoline]-2,2',5-trione and 1-(3-pyridylmethyl)-5,7-dichloroindoline-2,3-dione is converted to 1'-(3-pyridylmethyl)-5', 7'-dichloro-spiro[imidazolidine-4,3'-indoline]-2,2',5-trione.

Compounds of the invention of formula I where X and Y are each hydrogen and Z is amino are best prepared by the alkylation of sodio-ethyl hydantoin-5-carboxylate with 2,4-dinitrochlorobenzene, followed by reductive cyclization in a conventional manner. This last step is usually accomplished by using iron powder in the presence of an acid such as hydrochloric acid or glacial acetic acid, generally in the presence of an aqueous alkanol medium at ambient to slightly elevated temperatures (e.g., ca. 20°–100° C.). C ompounds of the invention of formula II wherein R' is hydrogen and R" is as previously defined are also best prepared in this manner by merely substituting the appropriate halonitro-disubstituted pyridine compound in place of 2,4-dinitrochlorobenzene in the first step of the reaction. In this way, the use of 3-nitro-4-chloropyridine ultimately leads to spiro-[imidazolidine-4,3'-(6-azaindoline)]-2,2',5-trione as the desired final product. Moreover, compounds of the invention of formula I where X and Y are both halogen (as previously defined) and Z is hydrogen may alternatively (and preferably) be prepared from the corresponding unsubstituted compounds wherein at least one of X and Y is hydrogen by means of direct halogenation techniques well known to those skilled in the field of synthetic organic chemistry. Additionally, these same manohalo starting materials (e.g., where X is halogen and Y and Z are both hydrogen) can be converted to the corresponding compounds where Y is nitro and amino, etc., by conventional procedure well-known to those skilled in the art (e.g., nitration and subsequent reduction, etc.). In the latter connection, the reduction step is preferably accomplished by using catalytic hydrogenation, e.g., by using a platinum, palladium or nickel catalyst and gaseous hydrogen, or by using sodium amalgam and the like. Lastly, compounds of the invention of formula II wherein R' is other than hydrogen can alternatively (and preferably) be prepared from the corresponding compounds where R' is hydrogen by the use of standard techniques well-known to those skilled in the art. For instance, the use of an appropriate reagent of the formula R'''X", where R''' is other than hydrogen or aryl and X" is a leaving group such as an aryl or alkylsulfonyloxy radical, in the presence of a base such as sodium hydride or sodium hydroxide ultimately leads to the formulation of compounds of formula II where R' is alkyl or aralkyl as previously defined.

The ketone starting materials (i.e., carbonyl ring compounds of structural formulae III–IV) required for preparing the desired final products of structural formulae I–II in the overall process of this invention are, for the most part, known compounds and are either readily available commercially, like isatin (2,3-indolinedione), 5-fluoroisatin, 5-chloroisatin and 5,7-dichloroisatin, etc., or else they can easily be synthesized by those skilled in the art starting from common chemical reagents and using conventional methods of organic synthesis. For instance, the 1-aralkyl-5-haloisatins are easily obtained by alkylating 5-fluoro or 5-chloroisatin with the appropriate aralkyl halide of choice (e.g., 3-chloromethylpyridine) in the presence of a base such as sodium hydride or potassium carbonate, while the corresponding 1-aryl-5-haloisatins are best synthesized by treatment of the appropriate diarylamine compound with oxalyl chloride, followed by ring-closure with aluminum chloride in the usual manner. In either case, the ultimate starting materials are both readily derived from readily available compounds.

Inasmuch as the spiro-oxindole imidazolinedione compounds of this invention all possess one asymmetric center, they may exist in separated d- and l-optically active forms, as well as in racemic or dl-mixtures. The present invention includes all these forms. For instance, an optically active isomer may be obtained by simply resolving the racemic mixture via the use of standard techniques well-known to those skilled in the art, e.g., by fractional crystallization of a spiro-oxindole imidazolidinedione salt derived from an optically active acid or base. Alternatively, the optically active isomers may be prepared by using the appropriate enantiomers as starting materials in the foregoing series of reactions.

The pharmaceutically acceptable acid addition salts of the spiro-oxindole imidazolidinedione base compounds of this invention are prepared by simply treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt is readily obtained.

The chemical bases which are used as reagents to prepare the pharmaceutically acceptable base salts of this invention are those which form non-toxic base salts with the herein described acidic spiro-oxindole imidazolidinedione compounds. These particular non-toxic base salts include those derived from such pharmacologically acceptable cations as sodium, potassium, calcium and magnesium, etc. These salts can easily be prepared by simply treating the aforementioned spiro-oxindole imidazolidinedione acidic compounds with an aqueous solution of the desired pharmacologically acceptable cation, and then evaporating the resulting solution to dryness while preferably being placed under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantitites of reagents are preferably employed in order to ensure completeness of reaction and maximum production of yields of the desired final product.

As previously indicated, the spiro-oxindole imidazolidinedione compounds of this invention are readily adapted to therapeutic use as aldose reductase inhibitors for the control of chronic diabetic complications, in view of their ability to reduce lens sorbitol levels in diabetic subjects to a statistically significant degree. For instance, 1'-(3-pyridylmethyl)-5',7'-dichloro-sprio-[imidazolidine-4,3'-indoline]-2,2',5-trione, a typical and preferred agent of the present invention, has been found to inhibit the formation of sorbitol levels in diabetic rats to a significantly high degree when given by the oral route of administration at dose levels ranging from 0.5 mg./kg. to 20 mg./kg. Furthermore, the herein described compounds of this invention can be administered by either the oral or parenteral routes of administration. In general, these compounds are ordinarily administered in dosages ranging from about 0.10 mg. to about 10 mg. per kg. of body weight per day, although variations will necessarily occur depending upon the weight and condition of the subject being treated and the particular route of administration chosen.

In connection with the use of the spiro-oxindole imidazolidinedione compounds of this invention for the treatment of diabetic subjects, it is to be noted that these compounds may be administered either alone or in combination with pharmaceutically acceptable carriers by either of the routes previously indicated, and that such administration can be carried out in either single or multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. In general, the compounds of the invention will be present in such dosage forms at concentration levels ranging from about 0.5% to about 90% by weight of the total composition to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various like combinations thereof.

For purposes of parenteral administration, solutions of these spiro-oxindole imidazolidinediones in sesame or peanut oil or in aqueous propylene glycol or N,N-dimethylformamide may be employed, as well as sterile aqueous solutions of the corresponding water-soluble, non-toxic mineral and organic acid addition salts or alkali or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art. Additionally, it is also possible to administer the aforesaid spiro-oxindole oxazolidinedione compounds topically via an appropriate ophthalmic solution applied dropwise to the eye.

The activity of the compounds of the present invention, as agents for the control of chronic diabetic complications, is determined by their ability to successfully pass one or more of the following standard biological or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

PREPARATION A

A solution consisting of 3.0 g. (0.014 mole) of ethyl ureidomalonate dissolved in 43 ml. of absolute ethanol was heated under reflux in a nitrogen atmosphere, while a 0.017 molar solution of sodium ethanolate (sodium in ethanol) while slowly added thereto over a period of 2.5 hours. Upon completion of this step, the resulting reaction mixture was cooled to room temperature (~20° C.) and the desired product collected by means of suction filtration and subsequently washed with two-20 ml. portions of absolute ethanol and one-20 ml. portion of absolute ether. In this manner, there was ultimately obtained pure sodio-ethyl hydantoin-5-carboxylate.

When the reaction was repeated using 10 g. of starting material (ethyl ureidomalonate) and 1.06 g. of sodium in 60 ml. of absolute ethanol, the yield of pure final product amounted to 7.53 g. (85%).

PREPARATION B

A mixture consisting of 20 g. (0.14 mole) of 3-nitro-4-hydroxypyridine, 33.3 g. of phosphorus pentachloride and 2 ml. of phosphorus oxychloride was heated in an oil both at 130° C. for a period of three hours. Upon completion of this step, the excess phosphorus oxychloride was removed from the spent reaction mixture by means of fractional distillation and the residual material was subsequently taken up in methylene chloride. The latter solution was then washed with saturated aqueous sodium bicarbonate solution, dried over anhydrous magnesium sulfate and filtered. Evaporation of the solvent from the resulting filtrate then gave the desired product, viz., 3-nitro-4-chloropyridine.

When the procedure was repeated using 2.8 g. (0.02 mole) of starting material (3-nitro-4-hydroxypyridine), the yield of pure final product amounted to 2.35 g. (74%).

PREPARATION C

A solution consisting of 20.2 g.(0.182 mole) of p-fluoroaniline and 22.1 g. (0.182 mole) of p-fluorobenzaldehyde dissolved in 100 ml. of ethanol was refluxed for a period of five minutes. Upon completion of this step, the spent reaction mixture was cooled to room temperature (~20° C.) and the desired product subsequently collected by means of suction filtration. A second crop of product was thereafter obtained by concentrating the resulting filtrate in vacuo. The total yield of pure 3-[(p-fluorophenyl)methylidene]pyridine amounted to 33 g. (84%).

To 11.0 g. of the above intermediate in 50 ml. of methanol, there were added 1.92 g. of sodium borohydride at room temperature. Upon completion of this step, the resulting reaction mixture was diluted with water, extracted with diethyl ether and the ethereal extracts subsequently dried over anhydrous magnesium sulfate and filtered. After removal of the drying agent by means of filtration and the solvent by means of evaporation under reduced pressure, there was ultimately obtained a crude residual product which thereafter crystallized from n-hexane to afford pure 3-[(p-fluorophenyl)aminomethyl]pyridine. The yield of pure product amounted to 8.6 g. (77%).

EXAMPLE 1

A solution consisting of 500 mg. (0.230 mole) of spiro-[imidazolidine-4,3'-indoline]-2,2', 5-trione [H. Otamasu et al., *Chem. Pharm. Bull.* (Tokyo), Vol. 23, No. 7, p.1431 (1975)] dissolved in 10 ml. of dioxane and 2 ml. of water was treated with chlorine gas by bubbling the gas through the mixture at room temperature (~20° C.) until saturation of same was complete with respect to said gas (this required a period of approximately two minutes). The course of the reaction was followed by means of thin layer chromatography (using acetone/hexane as the eluant) in order to ensure that no dichlorination occurred. Upon completion of this step, the reaction mixture was diluted with sodium sulfite solution and extracted with ethyl acetate to ultimately afford pure 5'-chloro-spiro-[imidazolidine-4,3'-indoline]-2,2',5-trione. The yield of pure product amounted to 150 mg. (26%).

A well-stirred mixture consisting of 300 mg. of 5'-chloro-spiro-[imidazolidine-4,3'-indoline]-2,2',5-trione, 48 ml. of glacial acetic acid and 16 ml. of fuming nitric acid was heated at 90° C. for a period of one-half hour. Upon completion of this step, the cooled reaction mixture was poured into water, partially neutralized with sodium bicarbonate solution and the resulting product subsequently collected by means of suction filtration. In this manner, there was ultimately obtained 2.05 mg. (58%) of pure 5'-chloro-7'-nitro-spiro-[imidazolidine-4,3'-indoline]-2,2',5-trione, m.p.>270° C.

A solution consisting of 80 mg. of 5'-chloro-7'-nitro-spiro-[imidazolidine-4,3'-indoline]-2,2',5-trione dissolved in 5 ml. of ethanol containing 0.5 ml. of concentrated hydrochloric acid was treated with 10 mg. of 10% palladium on carbon catalyst and stirred in a hydrogen atmosphere at room temperature for a period of one hour. The resulting reaction mixture was then filtered thru filter-cel to remove the catalyst, which was thereafter washed with ethanol, and the combined washings and filtrate were subsequently concentrated in vacuo to afford a crude residual product. Recrystallization of the latter material from chloroform then gave pure 5'-chloro-7'-amino-spiro-[imidazolidine-4,3'-indolidine]-2,2',5-trione as the hydrochloride salt. The yield of pure material amounted to 56 mg. (68%). The pure product was characterized by means of high resolution mass spectroscopy (m/e, 266.0125; theory, 266.0177) and nuclear magnetic resonance data.

EXAMPLE 2

A mixture consisting of 1.0 g. of a 50% dispersion of sodium hydride in mineral oil that had been covered with 50 ml. of dimethylformamide was treated with 2.16 g. of 5,7-dichloroindoline-2,3-dione (5,7-dichloroisatin) by adding the latter material slowly thereto in small portions. This was then followed by the addition of 1.64 g. of 3-pyridylmethylchloride and the resulting reaction mixture was heated at 90° C. for a period of one hour. Upon completion of this step, the spent reaction mixture was diluted with water, acidified and then extracted with ethyl acetate, followed by basification of the organic layer with aqueous sodium bicarbonate solution. The latter aqueous solution was then extracted with ethyl acetate, and the resulting organic layer saved and subsequently concentrated in vacuo to afford a crude residual product. Recrystallization of the latter material from diethyl ether/ethyl acetate then gave 1.7 g. (55%) of pure 1-(3-pyridylmethyl)-5,7-dichloroindoline-2,3-dione.

A mixture of consisting of 1.53 g. of 1-(3-pyridylmethyl)-5,7-dichloroindoline-2,3-dione, 390 mg. of potassium cyanide and 1.86 g. of powdered ammonium carbonate in 40 ml. of 50% aqueous methanol was heated in an oil bath at 80° C. for a period of one-half hour. At the end of this time, the spent reaction mixture was cooled in an ice bath, quenched (i.e., acidified) with concentrated hydrochloric acid and diluted with additional water. After extracting the resulting aqueous solution with ethyl acetate, there were obtained several organic extracts that were later combined and subsequently dried over anhydrous magnesium sulfate to give a clear solution. Upon removal of the drying agent by means of filtration and the solvent by means of evaporation under reduced pressure, there was ultimately obtained a residual material that was later chromatographed over 30 g. of silica gel using ethyl acetate as the eluant. The appropriate fractions were then combined and subsequently concentrated in vacuo to afford a pure solid residual material. Recrystallization of the latter material from ethanol/hexane then gave 750 mg. of pure 1'-(3-pyridymethyl)-5',7'-dichloro-spiro-[imidazolidine-4,3'-indoline]-2,2',5-trione, m.p. 274° C.(decomp.). The pure product was further characterized by means of mass spectroscopy and nuclear magnetic resonance data.

EXAMPLE 3

To a stirred solution consisting of 1.1 ml. of oxalyl chloride in 40 ml. of methylene chloride at 0° C., there was added in a dropwise fashion a clear solution consisting of 3-[(p-fluorophenyl)aminomethyl]pyridine (the product of Preparation C) dissolved in 30 ml. of methylene chloride. After stirring at room temperature ($\sim$20° C.) for five minutes, 2.7 g. of anhydrous aluminum chloride was added to the mixture in one full portion with the aid of vigorous agitation. The resulting reaction mixture was then refluxed for a period of 15 minutes. At the end of this time, the spent mixture was poured into ice water in order to decompose the aluminum chloride, neutralized with sodium bicarbonate and extracted with ethyl acetate. After drying the organic extract over anhydrous magnesium sulfate, the solvent was removed in vacuo and the residue crystallized from ethyl acetate to afford 1.25 g. (50%) of pure 1-(3-pyridylmethyl)-5-fluoroindoline-2,3-dione.

A mixture consisting of 1.024 g. of 1-(3-pyridylmethyl)-5-fluoroindoline-2,3-dione, 390 mg. of potassium cyanide and 1.86 g. of powdered ammonium carbonate in 40 ml. of 50% aqueous methanol was heated in an oil both at 80° C. for a period of 20 minutes. At the end of this time, the spent reaction mixture was cooled in an ice bath, acidified with glacial acetic acid and diluted with additional water. After extracting the resulting aqueous solution with ethyl acetate, there were obtained several organic extracts that were later combined and suesequently dried over anhydrous magnesium sulfate to give a clear solution. Upon removal of the drying agent by means of filtration and the solvent by means of evaporation under reduced pressure, there was ultimately obtained a residual material that was later crystallized from ethyl acetate to afford 700 mg. (43%) of pure 1'-(3-pyridylmethyl)-5'-fluorospiro-[imidazolidine-4,3'-indoline]-2,2',5-trione. Recrystallization from methanol in the presence of activated carbon then gave an analytically pure sample, m.p. 202° C.(decomp.). The pure product was further characterized by means of mass spectroscopy and nuclear magnetic resonance data.

EXAMPLE 4

A solution consisting of 2.0256 g. (0.01 mole) of 2,4-dinitrochlorobenzene and 2.384 g. (0.014 mole) of sodio-ethyl hydantoin-5-carboxylate (the product of Preparation A) dissolved in 10 ml. of dimethylformamide was allowed to stand at room temperature ($\sim$20° C.) for a period of ca. 0.5–1.0 hour. Upon completion of this step, the spent reaction mixture was diluted with 50 ml. of water and extracted with two-25 ml. portions of ethyl acetate. The separated organic extracts were then combined and subsequently dried over anhydrous magnesium sulfate. After removal of the drying agent by means of filtration and the solvent by means of evaporation under reduced pressure, there was ultimately obtained pure ethyl 5-(2,4-dinitrophenyl)hydantoin-5-carboxylate as the desired product.

A solution consisting of 0.3142 g. (0.001 mole) the above intermediate dissolved in 50 ml. of 50% aqueous ethanol was then brought to a rapid reflux, followed by the addition of 0.3351 g. (0.006 mole) of iron powder and 1 drop of concentrated hydrochloric acid to the stirred mixture. The resulting reaction mixture was then stirred mechanically for a period of ca. 0.5–1.0 hour. Upon completion of this step, the spent reaction mixture was neutralized with saturated aqueous sodium bicarbonate solution and the solvents were thereafter evaporated from the neutralized solution. In this manner, there was ultimately obtained pure 6'-amino-spiro-[imidazolidine-4,3'-indoline]-2,2',5-trione (m.p.>275° C.).

When the reaction was repeated using 2.63 g. of pure ethyl 5-(2,4-dinitrophenyl)hydantoin-5-carboxylate as starting material and with the aid of mechanical stirring for a period of three hours, the yield of the desired final product amounted to 1.5 g. (77%). The pure product was further characterized by means of mass spectroscopy and nuclear magnetic resonance data.

EXAMPLE 5

A solution consisting of 639.2 mg. (0.00403 mole) of 3-nitro-4-chloropyridine (the product of Preparation B) and 1.0288 g. (0.0053 mole) of sodio-ethyl hydantoin-5-carboxylate (the product of Preparation A) dissolved in 10 ml. of dimethylformamide was allowed to stand at room temperature ($\sim$20° C.) overnight for a period of approximately 16 hours with the aid of mechanical stirring. Upon completion of this step, the solvent was evaporated from the mixture and the crude residual material was thereafter dried under a high vacuum and eventually crystallized from methylene chloride to afford 525 mg. of pure ethyl 5-(3-nitro-4-pyridyl)hydantoin-5-carboxylate, m.p. 203.5°–204.5° C.

When the reaction was repeated using 2.35 g. of 3-nitro-4-chloropyridine as starting material and 3.74 g. of sodio-ethyl hydantoin-5-carboxylate as the alkylating agent, the yield of pure product obtained amounted to 3.83 g. (88.3%).

A mixture consisting of 158.5 mg. (0.00054 mole) of ethyl 5-(3-nitro-4-pyridyl)hydantoin-5-carboxylate, 335.1 mg. of iron powder and 5 ml. of glacial acetic acid was heated to 100° C. and then cooled to ca. 65° C. The reaction was complete in approximately 10–15 minutes. Upon completion of this step, the spent reaction mixture was filtered thru filter-cel in order to remove the unwanted solids and the resulting filtrate was subsequently evaporated under reduced pressure to finally afford pure spiro-[imidazolidine-4,3'-(6-azaindoline)]-2,2',5-trione as the desired final product. The yield of pure material melting at 265° C. (decomp.) amounted to 80 mg. (68%). The pure product was further characterized by means of mass spectroscopy and nuclear magnetic resonance data.

EXAMPLE 6

The following spiro-oxindole imidazolidinedione final products of Examples 1–5, respectively, were tested at a concentration level of $10^{-6}M$ for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In every case, the substrate employed was partially purified aldose reductase enzyme obtained from calf lens. The results obtained with each compound are expressed below in terms of their percent inhibition of enzyme activity (%) with respect to the particular concentration level chosen ($10^{-6}$M):

| Compound | % Inhibition at $10^{-6}$ M |
|---|---|
| Product of Example 1 | 72 |
| Product of Example 2 | 81 |
| Product of Example 3 | 71 |
| Product of Example 4 | 27 |
| Product of Example 5 | 49 |

I claim:

1. A compound selected from the group consisting of spiro-hydantoin derivatives of the formulae:

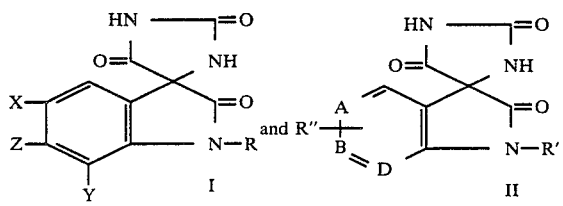

and the pharmaceutically acceptable salts thereof, wherein

X and Y are each hydrogen, fluorine, chlorine, bromine, nitro or amino;

Z is hydrogen or amino, with the proviso that at least one of X, Y and Z is amino and with the further proviso that said Z is always other than amino when at least one of X and Y is other than hydrogen;

R is hydrogen;

=A—B=D— of formula II represents =N—CH=CH—, =CH—CH=N— or =CH—N=CH—;

R' is a member selected from the group consisting of hydrogen, alkyl having from one to four carbon atoms, aryl and aralkyl having up to three carbon atoms in the alkyl moiety wherein each of said aryl moieties is chosen from the group consisting of pyridyl, thienyl, phenyl and mono and di-substituted phenyl, with each ring substituent being chosen from the group consisting of fluorine, chlorine, bromine, alkyl and alkoxy each having up to four carbon atoms and trifluoromethyl; and R" is hydrogen, hydroxy, fluorine, chlorine, alkyl or alkoxy each having up to four carbon atoms or trifluoromethyl.

2. A compound as claimed in claim 1 of the formula I wherein X is chlorine, Y is amino and Z is hydrogen.

3. A compound as claimed in claim 1 of the formula I wherein X and Y are each hydrogen and Z is amino.

4. A compound as claimed in claim 1 of the formula II wherein =A—B=D— is =N—CH=CH—.

5. A compound as claimed in claim 1 of the formula II wherein =A—B=D— is =CH—CH=N—.

6. A compound as claimed in claim 1 of the formula II wherein =A—B=D— is =CH—N=CH—.

7. A compound as claimed in claim 6 wherein R' and R" are each hydrogen.

8. A compound as claimed in claim 6 wherein R' is alkyl having from one to four carbon atoms and R" is hydrogen.

9. A compound as claimed in claim 8 wherein R' is isopropyl.

10. A compound as claimed in claim 6 wherein R' is mono-substituted phenylalkyl having up to three carbon atoms in the alkyl moiety and R" is hydrogen.

11. A compound as claimed in claim 10 wherein R' is p-chlorobenzyl.

12. A compound as claimed in claim 6 wherein R' is di-substituted phenylalkyl having up to three carbon atoms in the alkyl moiety and R" is hydrogen.

13. A compound as claimed in claim 12 wherein R' is 3,4-dichlorobenzyl.

14. A compound as claimed in claim 6 wherein R' is mono-substituted phenylalkyl having up to three carbon atoms in the alkyl moiety and R" is alkyl having from one to four carbon atoms.

15. A compound as claimed in claim 14 wherein R' is p-fluorobenzyl and R" is methyl.

16. A compound as claimed in claim 6 wherein R' is mono-substituted phenyl and R" is hydrogen.

17. A compound as claimed in claim 16 wherein R' is p-fluorophenyl.

18. A pharmaceutical composition suitable for oral administration comprising a pharmaceutically acceptable carrier and a compound as claimed in claim 1 in an amount effective for the treatment of diabetes-associated chronic complications.

19. A method for treating a diabetic host to prevent or alleviate chronic complications arising in said host, which comprises administering to said diabetic host an effective amount of a compound as claimed in claim 1.

* * * * *